US 9,670,199 B2

(12) United States Patent
Dosa et al.

(10) Patent No.: US 9,670,199 B2
(45) Date of Patent: Jun. 6, 2017

(54) ERGOLINE DERIVATIVES AS DOPAMINE RECEPTOR MODULATORS

(71) Applicant: REGENTS OF THE UNIVERSITY OF MINNESOTA, Minneapolis, MN (US)

(72) Inventors: Peter Dosa, Minneapolis, MN (US); Suck Won Kim, Minneapolis, MN (US); Michael Walters, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 14/443,576

(22) PCT Filed: Nov. 19, 2013

(86) PCT No.: PCT/US2013/070806
§ 371 (c)(1),
(2) Date: May 18, 2015

(87) PCT Pub. No.: WO2014/078857
PCT Pub. Date: May 22, 2014

(65) Prior Publication Data
US 2015/0307486 A1    Oct. 29, 2015

Related U.S. Application Data

(60) Provisional application No. 61/728,121, filed on Nov. 19, 2012.

(51) Int. Cl.
| | | |
|---|---|---|
| A61K 31/48 | (2006.01) |
| C07D 457/06 | (2006.01) |
| C07D 457/02 | (2006.01) |
| C07D 457/04 | (2006.01) |

(52) U.S. Cl.
CPC ......... *C07D 457/06* (2013.01); *C07D 457/02* (2013.01); *C07D 457/04* (2013.01)

(58) Field of Classification Search
USPC .................. 514/288, 232.8; 546/69; 544/125
See application file for complete search history.

(56) References Cited

U.S. PATENT DOCUMENTS 4,526,892 A * 7/1985 Salvati .................. C07D 457/06
                                                              514/288
2008/0275240 A1   11/2008  Wang et al.
2012/0329806 A1   12/2012  Cook et al.

FOREIGN PATENT DOCUMENTS

| CA | 2587880 A1 | 11/2008 |
| CN | 1076196 A | 9/1993 |
| DE | 237837 A1 | 7/1986 |
| EP | 0389068 A2 | 6/1986 |

OTHER PUBLICATIONS

Ben Zion, et al., "Polymorphisms in the dopamine D4 receptor gene (DRD4) contribute to individual differences in human sexual behavior: desire, arousal and sexual function", Mol Psychiatry 11, 782-786 (2006).
Bernardi, et al., "Derivati della ergolina. Nota *. Derivati della D, 6-metil-8.beta.-aminometil-10.alpha.-erg olina", Gazetta Chimica Italiana vol. 94, 936-946 (1964). [English Abstract.].
Brambilla, et al., "Synthesis and Nidtion Activity of a New Class of Ergoline Derivatives", European Journal of Medicinal Chemistry, vol. 24, 421-426 (1989).
Brioni, et al., "Activation of dopamine D4 receptors by ABT-724 induces penile erection in rats", Proc Natl Acad Sci USA, 101 (17), 6758-6763 (2004).
Castillo, et al., "Cushing's disease in dogs: cabergoline treatment", Research in Veterinary Science 85, 26-35 (2008).
Cerny, et al., "Mutterkornalkaloide 39. Mitteilung: Beitragzur Herstellung von D-Dihydrolyserg (I) - saure und ihres Methylesters", XP-002718843 Coll. Czech. Chem. Comm. vol. 47 (2), 740-741 (1982).
Chiba, et al., "Cabergoline, a dopamine receptor agonist, has an antidepressant-like property and enhances brain-derived neurotrophic factor signaling", Psychopharmacology 211, 291-301 (2010).
De Rosa, et al., "Cabergoline treatment rapidly improves gonadal function in hyperprolactinemic males: a comparison with bromocriptine", Eur J Endocrinol 138, 286-293 (1998).
Dosa, et al., "Synthesis of novel analogs of cabergoline: improving cardiovascular safety by removing 5-HT2B receptor agonism", ACS Med Chem Lett 4 (2), 254-258 (2013).
Gornemann, et al., "Characterization of the molecular fragment that is responsible for agonism of pergolide at serotonin 5-Hydroxytryptamine2B and 5-Hydroxytryptamine2A receptors", J Pharmacol Exp Ther 324 (3), 1136-1145 (2008).

(Continued)

*Primary Examiner* — Charanjit Aulakh
(74) *Attorney, Agent, or Firm* — Viksnins Harris & Padys PLLP

(57) ABSTRACT

The invention provides compounds of formula I:

wherein $R^1$-$R^4$ have any of the values defined in the specification, and salts thereof. The compounds are useful as dopamine receptor modulators for the treatment of diseases where modulation of dopamine receptors is implicated (e.g. sexual dysfunction, prolactinoma, Parkinson's disease, and Cushings disease).

10 Claims, No Drawings

(56) References Cited

OTHER PUBLICATIONS

Guptarak, et al., "Role of 5-HT(1A) receptors in fluoxetine-induced lordosis inhibition", Hormones and Behavior 58, 290-296 (2010).
Jacobs, et al., "The Ergot Alkaloids. XI. Isomeric Dihydrolysergic Acids and the Structure of Lysergic Acid", J. Biol. chem, vol. 115, 227-237 (1936).
Kekewska, et al., "The Bulky N(6) Substituent of Cabergoline is Responsible for Agonism of this Drug at 5-Hydroxytryptamine (5-HT)2A and 5-HT2B Receiptors and Thus is a Determinant of Valvular Heart Disease", Journal of Pharmacology and Experimental Therapeutics vol. 338 (1), 381-391 (2011).
Kvernmo, et al., "A review of the receptor-binding and pharmacokinetic properties of dopamine agonists", Clinical Therapeutics 28, 1065-1078(2006).
Millan, et al., "Differential actions of antiparkinson agents at multiple classes of monoaminergic receptor. I. A multivariate analysis of the binding profiles of 14 drugs at 21 native and cloned human receptor subtypes", Journal of Pharmacology and Experimental Therapeutics 303, 791-804 (2002).
Newman-Tancredi, et al., "Differential actions of antiparkinson agents at multiple classes of monoaminergic receptor. III. Agonist and antagonist properties at serotonin, 5-HT(1) and 5-HT(2), receptor subtypes", Journal of Pharmacology and Experimental Therapeutics 303, 815-822 (2002).
Nickel, et al., "Cabergoline treatment in men with psychogenic erectile dysfunction: a randomized, double-blind, placebo-controlled study", Int J Impot Res 19, 104-107 (2006).
Odin, et al., "Efficacy and safety of high-dose cabergoline in Parkinson's disease", Acta Neurologica Scandinavica 113, 18-24 (2006).
Patent Cooperation Treaty, International Searching Authority, Search Report and Written Opinion for PCT/US2013/070806, 11 pages, Feb. 3, 2014.
Petrossians, et al., "Medical treatment in Cushing's syndrome: dopamine agonists and cabergoline", Neuroendocrinology 92, 116-119 (2010).
Roth, et al., "Drugs and valvular heart disease", N Engl J Med 356, 6-9 (2007).
Rothman, et al., "Evidence for possible involvement of 5-HT(2B) receptors in the cardiac valvulopathy associated with fenfluramine and other serotonergic medications", Circulation 102, 2836-2841 (2000).
Safarinejad, et al., "Salvage of sildenafil failures with cabergoline: a randomized, double-blind, placebo-controlled study", Int J Impot Res 18, 550-558 (2006).
Schade, et al., "Dopamine agonists and the risk of cardiac-valve regurgitation", New England Journal of Medicine 356, 29-38 (2007).
Schreier, et al., "211. Xur Stereochemie der Mutterkornalkaloide vom Agroclavin-und Elymoclavin-Typus", Helv. Chim. Acta, vol. 41 (7), 1984-1997 (1958).
Stadler, et al., "162. Eine Einfache Veresterungsmethode im Eintopf-Verfahren", Helv. Chim. Acta., vol. 61 (5), 1675-1681 (1978). [English Summary.].
Stoll, et al., "101. Uber die Alkylierung der rac. Dihydro-nor-lysergsauren und Berichtigung zur 32. Mitteilung dieser Reihe", Helv. Chim. Acta, vol. 37 (3), 814-820 (1954).
Stoll, et al., "189. Uber die vierte isomere Dihydro-lysergsaure und eine neuartige Epimerisierungsreaktion. 32. Mitteilung uber Mutterkornalkaloide", Helvetica Chimica Acta vol. 36 (6), 1512-1526 (1953).
Stoll, et al., "49. Amide der stereoisomeren Lysergsauren und Dihydro-lysergsauren", Helv. Chim. Acta, vol. 38 (3), 421-433 (1955).
Stoll, et al., "55. Synthese der optisch aktiven Dihydro-lysergsauren", Helv. Chim. Acta, vol. 33 (2), 375-388 (1950).
Stoll, et al., "84. Die Dihydroderivate der rechtsdrenhenden Mutterkornalkaloide", Helv. Chim. Acta, vol. 29 (3), 635-653 (1946).
Stutz, et al., "Ergot Alkaloids. New Ergolines as Selective Dopaminergic Stimulants", J. Med. Chem., vol. 21 (8), 754-767 (1978).
Sukoff Rizzo, et al., "5-HT(1A) receptor antagonism reverses and prevents fluoxetine-induced sexual dysfunction in rats", International Journal of Neuropsychopharmacology 12, 1045-1053 (2009).
Takahashi, et al., "Addition of a dopamine agonist, cabergoline, to a serotonin-noradrenalin reuptake inhibitor, milnacipran as a therapeutic option in the treatment of refractory depression: two case reports", Clin Neuropharmacol. 26 (5), 230-232 (2003).
Verhelst, et al., "Cabergoline in the treatment of hyperprolactinemia: a study in 455 patients", J Clin Endocrinol Metab 84, 2518-2522 (1999).
Vilar, et al., "Effectiveness of cabergoline in monotherapy and combined with ketoconazole in the management of Cushing's disease", Pituitary 13, 123-129 (2010).
Voigt, et al., "Dihydrochanoclavine, Partialsynthese und biochemische Cyclisierung bei Claviceps purpurea Tul.", Pharmazie vol. 26, 494-503 (1971).
Yamatodani, et al., "On Reduction of Agroclavine and Elymoclavine with Sodium and n-Butanol, Bull. Agr. Chem. soc. Japan, vol. 20, 95 (1956)."
Zhang, et al., "Suppression of prolactin expression by cabergoline requires prolactin regulatory element-binding protein (PREB) in GH3 cells", Horm Metab Res 42, 557-561 (2010).
Jensen, et al., "N-desalkylquetiapine, a potent norepinephrine reuptake inhibitor and partial 5-HT1A agonist, as a putative mediator of quetiapine's antidepressant activity", Neuropsychopharmacology 33, 2303-2312 (2007).
McCall, et al., "Sumanirole, a Highly Dopamine D2-Selective Receptor Agonist: In Vitro and in Vivo Pharmacological Characterization and Efficacy in Animal Models of Parkinson's Disease", Journal of Pharmacology and Experimental Therapeutics, vol. 314 (3), 1248-1256 (2005).
Roth, "Assay Protocol Book, Version II", Department of Pharmacology, University of North Carolina at Chapel Hill, National Institue of Mental Health Psychoactive Drug Screening Progam (NIMH PDSP), 305 pages (Mar. 2013).

* cited by examiner

ERGOLINE DERIVATIVES AS DOPAMINE RECEPTOR MODULATORS

PRIORITY OF INVENTION

This application claims priority to U.S. Provisional Application No. 61/728,121 that was filed on Nov. 19, 2012. The entire content of this provisional application is hereby incorporated herein by reference.

BACKGROUND OF THE INVENTION

Cabergoline is a dopamine agonist that has been used clinically to treat prolactinomas, Parkinson's disease, and Cushing's disease and has been reported to have positive effects in patients suffering from depression (see Verhelst, J., et al. *J Clin Endocrinol Metab* 1999, 84, 2518; Odin, P., et al. *Acta Neurologica Scandinavica* 2006, 113, 18; Petrossians, P., et al. *Neuroendocrinology* 2010, 92, 116; Vilar, L., et al. *Pituitary* 2010, 13, 123; Castillo, V. A., et al. *Research in Veterinary Science* 2008, 85, 26; Takahashi, H., et al. *Clin. Neuropharmacol.* 2003, 26, 230; and Chiba, S., et al. *Psychopharmacology* 2010, 211, 291. Cabergoline is also used clinically to treat patients suffering from male sexual dysfunction, especially those with elevated prolactin levels (see Nickel, M., et al. *Int J Impot Res* 2006, 19, 104; De Rosa, M., et al. *Eur J Endocrinol* 1998, 138, 286; and Safarinejad, M. R. *Int J Impot Res* 2006, 18, 550). An elevated level of prolactin is a known risk factor for sexual dysfunction and cabergoline lowers the level of this hormone by binding to $D_2$ receptors in the pituitary and inhibiting prolactin synthesis (see Zhang, W., et al. *Horm Metab Res* 2010, 42, 557). Cabergoline is also an agonist at the $D_4$ and $5\text{-}HT_{1A}$ receptors, both of which are believed to play important roles in regulating sexual function both in males and females (see Millan, M. J., et al. *Journal of Pharmacology and Experimental Therapeutics* 2002, 303, 791; Kvernmo, T., et al., *Clinical Therapeutics* 2006, 28, 1065; Newman-Tancredi, A., et al. *Journal of Pharmacology and Experimental Therapeutics* 2002, 303, 815; Brioni, J. D., et al. *Proceedings of the National Academy of Sciences of the United States of America* 2004, 101, 6758; Guptarak, J., et al. *Hormones and Behavior* 2010, 58, 290; Ben Zion, I. Z, et al. *Mol Psychiatry* 2006, 11, 782; and Sukoff Rizzo, S. J., et al. *The International Journal of Neuropsychopharmacology* 2009, 12, 1045).

Unfortunately, cabergoline is also a potent agonist of the $5\text{-}HT_{2B}$ receptor (with a reported $K_i$ of 1.2 nM) and, like other $5\text{-}HT_{2B}$ agonists such as nor-dexfenfluramine, is known to cause cardiac-valve regurgitation (CVR) in patients. This potentially fatal complication has greatly limited the clinical use of cabergoline, especially in indications requiring high doses of the drug (see Newman-Tancredi, A., et al. *Journal of Pharmacology and Experimental Therapeutics* 2002, 303, 815; Rothman, R. B., et al. *Circulation* 2000, 102, 2836; Roth, B. L. *N Engl J Med* 2007, 356, 6; and Schade, R, et al. *New England Journal of Medicine* 2007, 356, 29.

In spite of the above reports, there is currently a need for therapeutic agents that have the useful therapeutic properties of cabergoline, but that lack the unwanted effects associated with agonism of the $5\text{-}HT_{2B}$ receptor.

SUMMARY OF THE INVENTION

Applicant has identified a series of compounds that have reduced agonist activity at the $5\text{-}HT_{2B}$ receptor. Representative compounds were found to modulate the $D_2$ receptor and/or the $D_4$ receptor. Accordingly, the compounds are useful for treating diseases and conditions wherein the activity of dopamine receptors is implicated (e.g. sexual dysfunction, prolactinomas, Parkinson's disease, and Cushings disease). Accordingly the invention provides a compound of formula I:

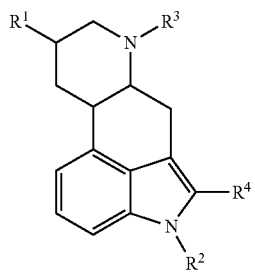

wherein:

$R^1$ is —C(=O)$NR_aR_b$, —C(=O)$OR_c$, $(C_1\text{-}C_6)$alkyl, $(C_1\text{-}C_6)$alkanoyl, $(C_1\text{-}C_6)$alkoxycarbonyl, or $(C_1\text{-}C_6)$alkanoyloxy, wherein any $(C_1\text{-}C_6)$alkyl, $(C_1\text{-}C_6)$alkanoyl, $(C_1\text{-}C_6)$alkoxycarbonyl, or $(C_1\text{-}C_6)$alkanoyloxy can optionally be substituted with one or more halo, hydroxy, $(C_1\text{-}C_6)$alkoxy, $(C_1\text{-}C_6)$alkanoyl, $(C_1\text{-}C_6)$alkoxycarbonyl, $(C_1\text{-}C_6)$alkanoyloxy, or $NR_dR_e$;

$R^2$ is H or $(C_1\text{-}C_6)$alkyl;

$R^3$ is methyl;

$R^4$ is H, halo, —C(=O)$NR_hR_k$, —C(=O)$OR_c$, $(C_1\text{-}C_6)$alkyl, $(C_1\text{-}C_6)$alkanoyl, $(C_1\text{-}C_6)$alkoxycarbonyl, or $(C_1\text{-}C_6)$alkanoyloxy, wherein any $(C_1\text{-}C_6)$alkyl, $(C_1\text{-}C_6)$alkanoyl, $(C_1\text{-}C_6)$alkoxycarbonyl, or $(C_1\text{-}C_6)$alkanoyloxy can optionally be substituted with one or more halo, hydroxy, $(C_1\text{-}C_6)$alkoxy, $(C_1\text{-}C_6)$alkanoyl, $(C_1\text{-}C_6)$alkoxycarbonyl, $(C_1\text{-}C_6)$alkanoyloxy, or $NR_mR_n$;

$R_a$ and $R_b$ are each independently H, $(C_1\text{-}C_6)$alkyl, —C(=O)$NR_fR_g$, or $(C_1\text{-}C_6)$alkanoyl, wherein any $(C_1\text{-}C_6)$alkyl or $(C_1\text{-}C_6)$alkanoyl can optionally be substituted with one or more $NR_fR_g$; or $R_a$ and $R_b$ together with the nitrogen to which they are attached form a heterocyclic ring;

$R_c$ is H, $(C_1\text{-}C_6)$alkyl, or aryl;

$R_d$ and $R_e$ are each independently H or $(C_1\text{-}C_6)$alkyl; or $R_d$ and $R_e$ together with the nitrogen to which they are attached form a heterocyclic ring; and $R_f$ and $R_g$ are each independently H or $(C_1\text{-}C_6)$alkyl; or $R_f$ and $R_g$ together with the nitrogen to which they are attached form a heterocyclic ring;

$R_h$ and $R_k$ are each independently H, $(C_1\text{-}C_6)$alkyl or $(C_1\text{-}C_6)$alkanoyl, wherein any $(C_1\text{-}C_6)$alkyl or $(C_1\text{-}C_6)$alkanoyl can optionally be substituted with one or more $NR_fR_g$; or $R_h$ and $R_k$ together with the nitrogen to which they are attached form a heterocyclic ring;

$R_m$ and $R_n$ are each independently H or $(C_1\text{-}C_6)$alkyl; or $R_m$ and $R_n$ together with the nitrogen to which they are attached form a heterocyclic ring;

or a salt thereof.

The invention also provides a pharmaceutical composition comprising a compound of formula I or a pharmaceutically acceptable salt thereof, and a pharmaceutically acceptable diluent or carrier.

The invention also provides a method for treating sexual dysfunction, prolactinoma, Parkinson's disease, depression, restless leg syndrome, or Cushings disease in an animal comprising administering a compound of formula I or a pharmaceutically acceptable salt thereof to the animal.

As described herein, sexual dysfunction includes, for example, decreased desire and orgasm disorders (endogenous or induced, e.g., induced by drugs (e.g., SSRIs, such as fluoxetine)). In certain embodiments, the sexual dysfunction is anorgasmia induced by administration of an SSRI (e.g., chronic administration of the SSRI).

The invention also provides a compound of formula I or a pharmaceutically acceptable salt thereof for use in medical therapy.

The invention also provides a compound of formula I or a pharmaceutically acceptable salt thereof for the prophylactic or therapeutic treatment of sexual dysfunction, prolactinoma, Parkinson's disease, depression, restless leg syndrome, or Cushings disease.

The invention also provides the use of a compound of formula I or a pharmaceutically acceptable salt thereof to prepare a medicament for treating sexual dysfunction, prolactinoma, Parkinson's disease, depression, restless leg syndrome, or Cushings disease in an animal (e.g. a mammal such as a human).

The invention also provides a method for modulating the activity of a dopamine receptor in an animal comprising administering a compound of formula I or a pharmaceutically acceptable salt thereof to the animal.

The invention also provides a compound of formula I or a pharmaceutically acceptable salt thereof for the prophylactic or therapeutic treatment of a disease associated with a dopamine receptor.

The invention also provides the use of a compound of formula I or a pharmaceutically acceptable salt thereof to prepare a medicament for modulating the activity of a dopamine receptor in an animal (e.g. a mammal such as a human).

The invention also provides processes and intermediates disclosed herein that are useful for preparing a compound of formula I or a salt thereof.

DETAILED DESCRIPTION

The following definitions are used, unless otherwise described: halo is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$ alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

The term "heterocyclic ring" refers to a saturated or a partially unsaturated (i.e., having one or more double and/or triple bonds within the ring) 3-15 membered mono-, bi-, or tricyclic group in which one or more (e.g. 1, 2, 3, or 4) ring atoms are heteroatoms independently selected from nitrogen, oxygen, and sulfur, the remaining ring atoms being carbon. In one embodiment, heterocyclic ring is a saturated or partially unsaturated 4-6 membered monocyclic group. A heterocyclic ring may be substituted with one or more (e.g. 1, 2 or 3) oxo groups and the sulfur and nitrogen atoms may also be present in their oxidized forms. Examples of heterocyclic rings include aziridine, azetadine, morpholino, piperazino, pyrrolidino or piperidino.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by isolation from biological sources, by synthesis from optically-active starting materials, by chiral synthesis, or by chromatographic separation using a chiral stationary phase.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, see-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_6)$alkanoyloxy can be acetoxy, propanoyloxy, butanoyloxy, isobutanoyloxy, pentanoyloxy, or hexanoyloxy; and aryl can be phenyl, indenyl, or naphthyl.

A specific compound of formula I is a compound of formula Ia:

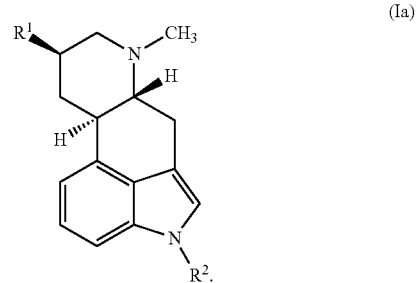

(Ia)

or a salt thereof. In one embodiment the invention provides a compound of formula I that is at least about 60, 75, 80, 90, 95, 98, or 99 percent enriched in the diasteromer of formula Ia.

A specific compound of formula I is a compound of formula Ib:

(Ib)

or a salt thereof.

A specific compound of formula I is a compound of formula Ic:

(Ic)

A specific compound of formula I is a compound of formula Id:

(Id)

A specific value for $R^1$ is —C(=O)$NR_aR_b$.
A specific value for $R^1$ is —C(=O)$OR_c$.
A specific value for $R^1$ is $(C_1-C_6)$alkyl, $(C_1-C_6)$alkanoyl, $(C_1-C_6)$alkoxycarbonyl, or $(C_1-C_6)$alkanoyloxy, wherein any $(C_1-C_6)$alkyl, $(C_1-C_6)$alkanoyl, $(C_1-C_6)$alkoxycarbonyl, or $(C_1-C_6)$alkanoyloxy can optionally be substituted with one or more halo, hydroxy, $(C_1-C_6)$alkoxy, $(C_1-C_6)$alkanoyl, $(C_1-C_6)$alkoxycarbonyl, $(C_1-C_6)$alkanoyloxy, or $NR_dR_e$.

A specific value for $R^1$ is $(C_1-C_6)$alkyl, optionally substituted with one or more $(C_1-C_6)$alkoxy.

A specific value for $R^1$ is dimethoxymethyl.

A specific value for $R^1$ is N-(3-dimethylaminopropyl)aminocarbonyl.

A specific value for $R^1$ is:

A specific value for $R^1$ is:

A specific value for $R^2$ is H.
A specific value for $R^2$ is $(C_1-C_6)$alkyl.
A specific value for $R^2$ is methyl.

In one embodiment of the invention $R_a$ and $R_b$ are each independently H, $(C_1-C_6)$alkyl or $(C_1-C_6)$alkanoyl, wherein any $(C_1-C_6)$alkyl or $(C_1-C_6)$alkanoyl can optionally be substituted with one or more $NR_fR_g$; or $R_a$ and $R_b$ together with the nitrogen to which they are attached form a morpholino, piperazino, pyrrolidino or piperidino.

In one embodiment of the invention $R_d$ and $R_e$ are each independently H or $(C_1-C_6)$alkyl; or $R_d$ and $R_e$ together with the nitrogen to which they are attached form a morpholino, piperazino, pyrrolidino or piperidino.

In one embodiment of the invention $R_f$ and $R_g$ are each independently H or $(C_1-C_6)$alkyl; or $R_f$ and $R_g$ together with the nitrogen to which they are attached form a morpholino, piperazino, pyrrolidino or piperidino.

In one embodiment of the invention $R_h$ and $R_k$ are each independently H, $(C_1-C_6)$alkyl or $(C_1-C_6)$alkanoyl, wherein any $(C_1-C_6)$alkyl or $(C_1-C_6)$alkanoyl can optionally be substituted with one or more $NR_fR_g$; or $R_a$ and $R_b$ together with the nitrogen to which they are attached form a morpholino, piperazino, pyrrolidino or piperidino.

In one embodiment of the invention $R_m$ and $R_n$ are each independently H or $(C_1-C_6)$alkyl; or $R_d$ and $R_e$ together with the nitrogen to which they are attached form a morpholino, piperazino, pyrrolidino or piperidino.

In one embodiment of the invention the compound is a partial agonist of 5-HT2B.

In one embodiment of the invention the compound is not an agonist or a partial agonist of 5-HT2B.

In one embodiment of the invention the compound is an antagonist of 5-HT2B.

In one embodiment the invention provides compounds that demonstrate less than 10% agonism of 5-HT2B in the functional assay reported by Porter, R. H. P., et al., *Br. J. Pharmacol.* 1999, 128, 13-20.

In one embodiment the invention provides compounds that demonstrate less than 5% agonism of 5-HT2B in the functional assay reported by Porter, R. H. P., et al., *Br. J. Pharmacol.* 1999, 128, 13-20.

Processes for preparing compounds of formula I are provided as further embodiments of the invention and are illustrated by the following procedures in which the meanings of the generic radicals are as given above unless otherwise qualified.

Compounds of the invention can be prepared as illustrated in Schemes 1 and 2.

Scheme 1. Synthesis of Compounds of the Invention

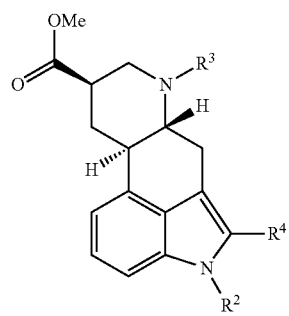

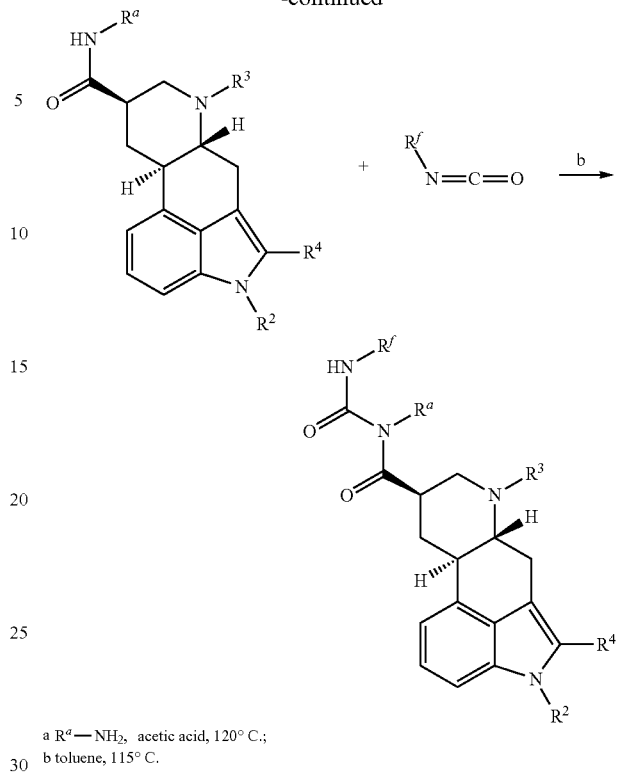

a $R^a$—$NH_2$, acetic acid, 120° C.;
b toluene, 115° C.

Scheme 2. Alternate Synthesis of Compounds of the Invention

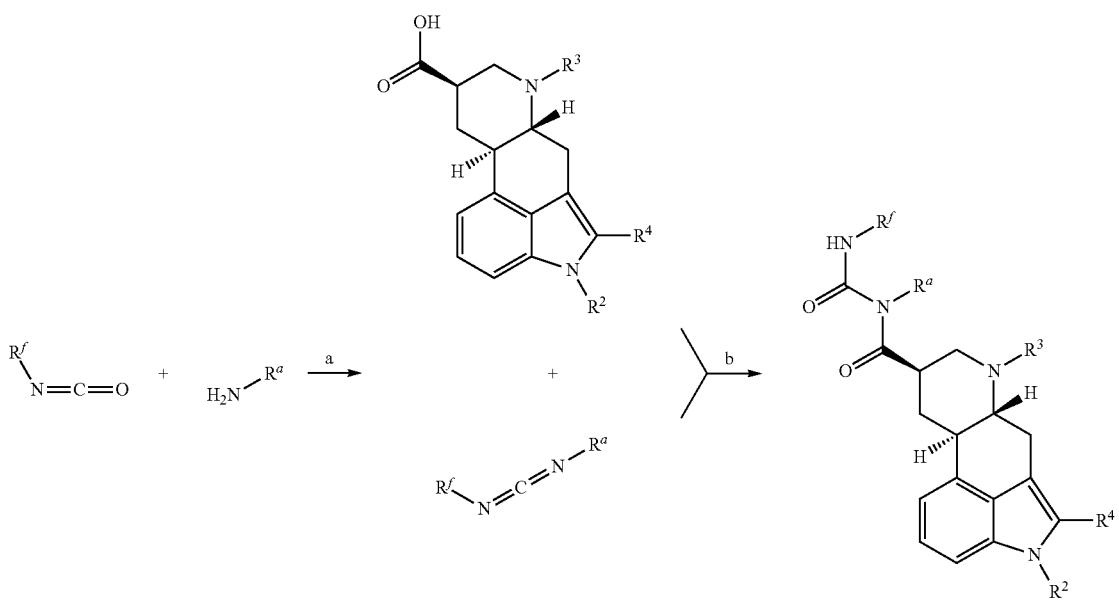

a i. $CH_2Cl_2$, 0° C.; ii. $NEt_3$, p-toluenesulfonyl chloride, reflux.
b $NEt_3$, $CH_2Cl_2$.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful for the treatment of depression. Examples of such agents include selective serotonin reuptake inhibitors such as for example, citalopram, dapoxetine, escitalopran, fluoxetine, fluvoxamine, indalpine, paroxetine, sertraline, vilazodone, and zimelidine.

The biological activity of representative compounds of the invention can be determined using a number of assays that are known. For example, 5-HT$_{2B}$ functional assays were performed following the procedure reported by Porter, R. H. P., et al., *Br. J. Pharmacol.* 1999, 128, 13-20. 5-HT$_{2B}$ binding assays were performed following the procedure reported by Choi, D.-S., et al., *FEBS Lett.* 1994, 352, 393-399, using an agonist radioligand. D$_2$ and D$_4$ functional assays were performed following the method reported by Jensen, N. H., et al., *Neuropsychopharmacology* 2007, 33, 2303-2312. Results from these assays are shown below.

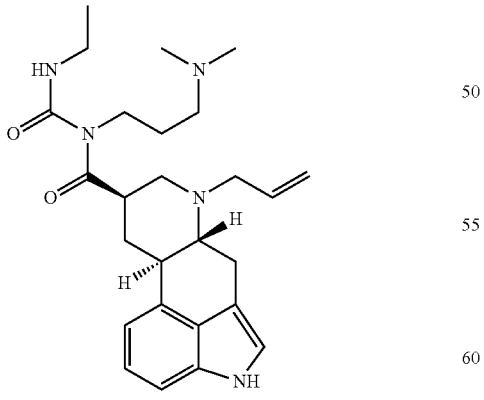

Cabergoline

5-HT$_{2B}$ binding assay, K$_i$ 1.4 nM
functional assay, EC$_{50}$ 13 nM
full agonist (E$_{max}$ 103%)

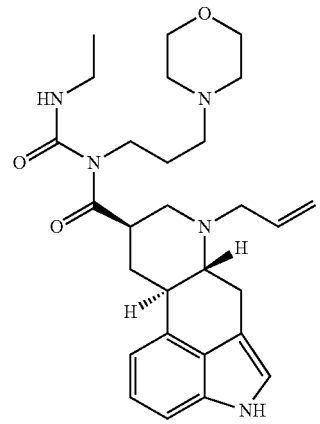

1

5-HT$_{2B}$ binding assay, K$_i$ 7.1 nM
functional assay, EC$_{50}$ 13 nM
full agonist (E$_{max}$ 106%)

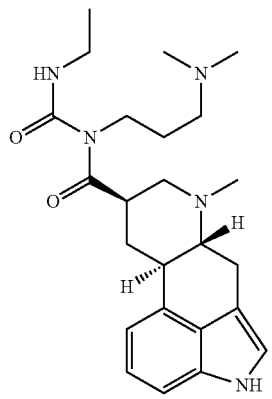

8

5-HT$_{2B}$ binding assay, K$_i$ 2.2 nM
functional assay, EC$_{50}$ 16 nM
partial agonist (E$_{max}$ 38%)

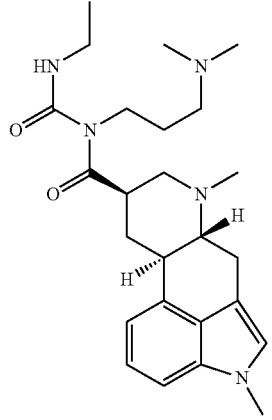

9

5-HT$_{2B}$ binding assay, K$_i$ 1.0 nM
functional assay, IC$_{50}$ 22 nM
antagonist (K$_B$ 5.6 nM)

13

-continued

14

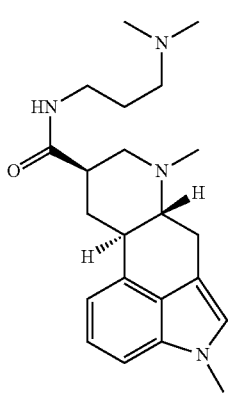

5-HT$_{2B}$ binding assay, K$_i$ 0.97 nM
functional assay, IC$_{50}$ 37 nM
antagonist (K$_B$ 9.3 nM)

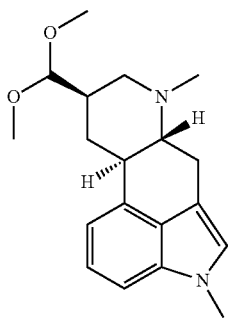

5-HT$_{2B}$ binding assay, K$_i$ 0.54 nM
functional assay, IC$_{50}$ 13 nM
antagonist (K$_B$ 3.3 nM)

Compound 1 and cabergoline were evaluated in a competitive binding assay at the 5-HT$_{2B}$ receptor against $^{125}$I-radiolabeled 2,5-dimethoxy-4-iodoamphetamine, as well as in a 5-HT$_{2B}$ functional assay using HTRF quantitation of IP1 accumulation. Compound 1 was not significantly less active at the 5-HT$_{2B}$ receptor than cabergoline. Both compounds were full agonists at the 5-HT$_{2B}$ receptor.

Compound 8 demonstrated similar potency as cabergoline and compound 1 in a 5-HT$_{2B}$ radioactive binding assay. A 5-HT$_{2B}$ functional assay showed that the change from a 6-allyl group to a 6-methyl group was not enough to completely eliminate 5-HT$_{2B}$ agonism, as compound 8 is a partial agonist, with an EC$_{50}$ of 16 nM and a E$_{max}$ of 38%.

Compounds 9 and 15 showed no agonism in 5-HT$_{2B}$ functional assays (n=6), while compound 14 showed minimal to no agonism in these assays (E$_{max}$<12% in all cases). All three compounds were potent antagonists against serotonin at the 5-HT$_{2B}$ receptor. These results demonstrated that it is indeed possible to synthesize compounds in which 5-HT$_{2B}$ agonism has been eliminated. Further investigation into 9 revealed that it is a full D$_4$ agonist, a potent but partial D$_2$ agonist (EC$_{50}$ 1.4 nM, E$_{max}$ 50%).

The invention will now be illustrated by the following non-limiting Examples.

EXAMPLES $^1$H NMR and $^{13}$C NMR Spectra were recorded on a Bruker 400 spectrometer. The $^1$H NMR data are reported as follows: chemical shift in parts per million downfield of tetramethylsilane (TMS), multiplicity (s=singlet, bs=broad singlet, d=doublet, t=triplet, q=quartet, quint=quintet and m=multiplet), coupling constant (Hz), and integrated value. The $^{13}$C NMR spectra were measured with complete proton decoupling. LC/MS analysis was carried out using a BEH C$_{18}$ column (2.1 mm×50 mm, 5 urn) on a Waters Acquity UPLC system with a Waters ZQ mass detector.

Example 1

Preparation of (5R,8R,10R)-6-Allyl-N-[3-(morpholino)propyl]-N-[(ethylamino)-carbonyl]ergoline-8-carboxamide (1)

a. N-(3-morpholinopropyl)-N'-ethylcarbodiimide (6)

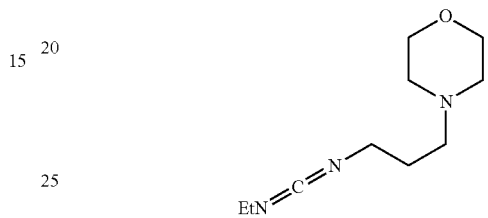

To a stirred solution of ethyl isocyanate (1.035 g, 14.56 mmol) in CH$_2$Cl$_2$ (7.5 mL) at 0° C. was added a solution of 3-morpholinopropylamine (2.017 g, 13.99 mmol) in CH$_2$Cl$_2$ (2.5 mL) dropwise over 15 min. After stirring an additional 15 min., triethylamine (5.0 mL, 35.87 mmol) was added followed by p-toluenesulfonyl chloride (3.06 g, 16.05 mmol) in 3 mL of CH$_2$Cl$_2$ (added over 5 min.). The mixture was heated to a gentle reflux for three hours. After cooling to rt, Na$_2$CO$_3$ (4.0 g, 37.7 mmol) and ice water (40 mL) were added. After stirring for 20 min., the organic layer was removed and the aqueous layer extracted with CH$_2$Cl$_2$ (30 mL). The combined organic layers were dried (Na$_2$SO$_4$), filtered, and concentrated under reduced pressure. The crude material was used without further purification in the next step.

b. (5R,8R,10R)-6-Allyl-N-[3-(morpholino)propyl]-N-[(ethylamino)carbonyl]-ergoline-8-carboxamide (1)

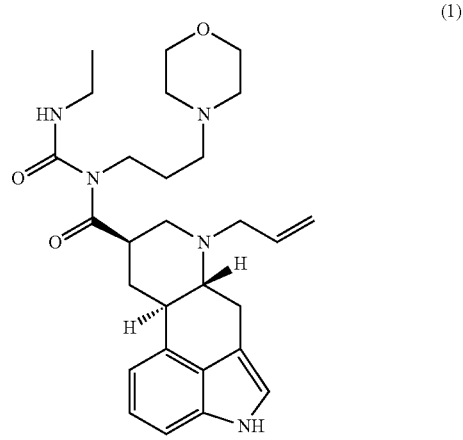 [SMILES: C=CCN1C[C@H](C(=O)N(CCCN2CCOCC2)C(=O)NCC)C[C@@H]2c3cccc4[nH]cc(c34)C[C@H]21]

(1)

Cabergolinic acid (2) was synthesized from cabergoline by the method of Wang and coworkers (Wang, Z.-X.; Li, Y.; Kondamreddy, M. et al. US 2007-797510, 2008). Cabergolinic acid (17.0 mg, 0.057 mmol) and N-(3-morpholinopropyl)-N'-ethylcarbodiimide (27.8 mg, 0.14 mmol) were stirred in $CH_2Cl_2$ (2 mL) and $NEt_3$ (0.020 mL) overnight. The reaction mixture was concentrated under reduced pressure and the resulting residue purified by chromatography (20% acetonitrile/water to 100% acetonitrile, $C_{18}$ column) to yield 8.6 mg white solid (30% yield). Compound 1 could also be synthesized from amide 4 according to the procedure for the synthesis of cabergoline developed by Ashford and coworkers (Ashford, S. W., et al., *J. Org. Chem.* 2002, 67, 7147-7150). $^1$H NMR (400 MHz, $CDCl_3$): 9.28 (bs, 1H), 7.91 (bs, 1H), 7.23-7.13 (m, 2H), 6.93-6.87 (m, 2H), 6.02-5.88 (m, 1H), 5.26 (d, J=17.0 Hz, 1H), 5.19 (d, J=9.8 Hz, 1H), 4.01-3.80 (m, 2H), 3.77-3.65 (m, 4H), 3.58 (dd, J=14.5, 5.9 Hz, 1H), 3.46 (dd, J=14.3, 3.9 Hz, 1H), 3.39-3.25 (m, 4H), 3.19-3.10 (m, 1H), 3.06-2.95 (m, 1H), 2.84-2.66 (m, 2H), 2.65-2.52 (m, 2H), 2.52-2.37 (m, 6H), 1.96-1.72 (m, 3H), 1.19 (t, J=7.3 Hz, 3H). LC/MS calculated for $C_{28}H_{39}N_5O_3+H^+$, 494.3; observed, 494.3.

Example 2

Preparation of (5R,8R,10R)-6-Allyl-N-[3-(morpholino)propyl]ergoline-8-carboxamide (4)

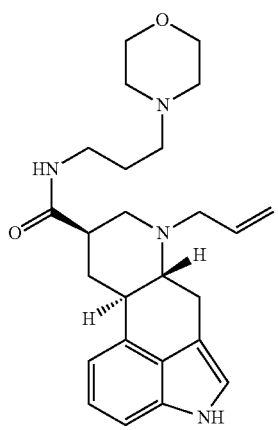

(4)

Cabergoline (40.0 mg, 0.089 mmol) and 3-morpholinopropylamine (0.400 mL, 2.74 mmol) were stirred under nitrogen in a sealed tube at 65° C. for 6 d. After cooling, the reaction mixture was dissolved in $CH_2Cl_2$ and extracted several times with phosphate buffer (pH 6.0) to remove excess 3-morpholinopropylamine. Each buffer extract was then extracted with $CH_2Cl_2$, and the organic phase extracted several times with additional phosphate buffer. The combined organic layers were dried under vacuum to afford 30 mg of compound 4 as a brown solid (80% yield). $^1$H NMR (400 MHz, $CDCl_3$): 8.00 (bs, 1H), 7.21-7.11 (m, 2H), 6.93-6.83 (m, 3H), 6.04-5.91 (m, 1H), 5.25 (d, J=17.1 Hz, 1H), 5.19 (d, J=10.1 Hz, 1H), 3.76-3.66 (m, 4H), 3.58 (dd, J=14.5, 5.7 Hz, 1H), 3.50-3.32 (m, 4H), 3.23-3.15 (m, 1H), 3.03-2.93 (m, 1H), 2.83-2.58 (m, 3H), 2.58-2.41 (m, 8H), 1.78-1.66 (m, 3H). $^{13}$C NMR ($CDCl_3$): 25.0, 26.7, 31.4, 39.3, 40.6, 44.1, 53.8, 55.7, 56.5, 58.0, 63.6, 67.1, 108.7, 111.8, 113.1, 117.8, 118.4, 123.1, 126.1, 132.9, 133.3, 133.8, 173.7. LC/MS calculated for $C_{25}H_{34}N_4O_2+H^+$, 423.3; observed, 423.4.

Example 3

Preparation of (5R,8R,10R)-6-Methyl-ergoline-8-carboxylic acid methyl ester (7)

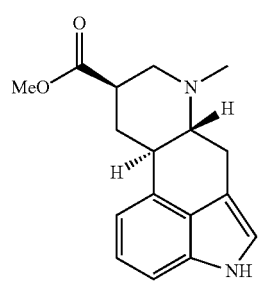

(7)

To a solution of dihydroergotamine methane sulfonate salt (617.5 mg, 0.908 mmol) in methanol (35 mL) was added NaOH (7.05 g, 176 mmol) in water (35 mL). The solution was stirred under nitrogen for 72 h, then diluted with dry methanol (250 mL) and acidified with concentrated $H_2SO_4$. After stirring for 48 h, the mixture was diluted with water (600 mL), neutralized with $K_2CO_3$, and extracted with $CH_2Cl_2$ (3×300 mL). The combined organic layers were dried ($MgSO_4$), filtered, and concentrated under reduced pressure. Flash chromatography ($CH_2Cl_2$/methanol/$NEt_3$ 94:5:1, silica gel) resulted in 143.7 mg of compound 7 as a slightly yellow solid (56% yield). $^1$H NMR (400 MHz, $CDCl_3$): 7.94 (bs, 1H), 7.21-7.12 (m, 2H), 6.95 (bd, J=6.2 Hz, 1H), 6.89 (bs, 1H), 3.74 (s, 3H), 3.41 (dd, J=14.7, 4.3 Hz, 1H), 3.32-3.21 (m, 1H), 3.04-2.89 (m, 3H), 2.77-2.62 (m, 1H), 2.51 (s, 3H), 2.36 (t, J=11.5 Hz, 1H), 2.24-2.16 (m, 1H), 1.60 (q, J=11.5 Hz, 1H). $^{13}$C NMR ($CDCl_3$): 26.9, 30.6, 40.2, 41.5, 43.1, 51.8, 58.7, 66.7, 108.7, 111.8, 113.3, 117.8, 123.2, 126.1, 132.7, 133.3, 174.4. LC/MS calculated for $C_{17}H_{20}N_2O_2+H^+$, 285.2; observed, 285.3.

Example 4

Preparation of 6-Methylcabergoline (8)

a. (5R,8R,10R)-6-Methyl-ergoline-8-carboxylic acid

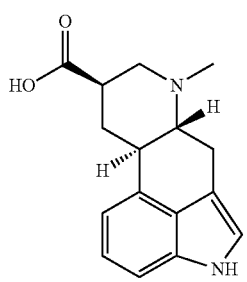 [SMILES: CN1C[C@H](C(=O)O)C[C@@H]2c3cccc4[nH]cc(c34)C[C@H]21]

To a solution of ester 7 (135.6 mg, 0.477 mmol) in methanol (5 mL) was added NaOH (183 mg) in water (0.30 mL). After 3 h, TLC analysis showed no remaining starting material. The reaction mixture was diluted with water (5 mL), acidified to pH 6 by slow addition of HCl, and then stirred at 0° C. for 90 min. The resulting solid was collected by filtration and washed with cold water. After drying, 91.9 mg of a white solid was obtained (71% yield). $^1$H NMR (400 MHz, (CD$_3$)$_2$SO): 12.34 (bs, 1H), 10.62 (bs, 1H), 7.12 (d, J=8.0 Hz, 1H), 7.01 (t, J=7.6 Hz, 1H), 6.97 (bs, 1H), 6.79 (d, J=7.1 Hz, 1H), 3.35-3.25 (m, 1H), 3.14-3.07 (m, 1H), 2.85-2.68 (m, 3H), 2.57-2.50 (m, 1H), 2.37 (s, 3H), 2.16 (t, J=11.4 Hz, 1H), 2.03-1.94 (m, 1H), 1.34 (q, J=13.0 Hz, 1H).

b. 6-Methylcabergoline (8)

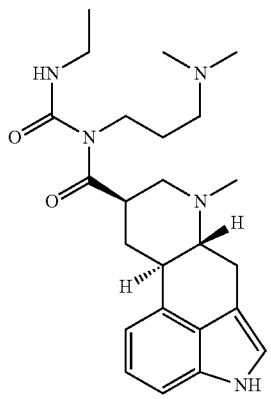 [SMILES: CCNC(=O)N(CCCN(C)C)C(=O)[C@@H]1C[C@@H]2c3cccc4[nH]cc(c34)C[C@H]2N(C)C1]

6-Methyl-ergoline-8-carboxylic acid (90 mg, 0.33 mmol) and N-(3-dimethylaminopropyl)-N'-ethylcarbodiimide HCl (83 mg, 0.43 mmol) were stirred in CH$_2$Cl$_2$ (5 mL) and NEt$_3$ (0.050 mL) overnight. The reaction mixture was concentrated under reduced pressure and the resulting residue purified by chromatography (5% acetonitrile/water to 100% acetonitrile, C$_{18}$ column) to yield 18.2 mg of compound 8 as a white solid (13% yield). $^1$H NMR (400 MHz, CDCl$_3$): 9.43 (bs, 1H), 7.91 (bs, 1H), 7.22-7.12 (m, 2H), 6.94-6.87 (m, 2H), 3.95-3.76 (m, 2H), 3.51-3.40 (m, 1H), 3.41 (dd, J=14.7, 4.3 Hz, 1H), 3.36-3.24 (m, 2H), 3.10 (dm, J=11.1 Hz, 1H), 3.07-2.97 (m, 1H), 2.85-2.79 (m, 1H), 2.75-2.65 (m, 1H), 2.51 (t, J=11.2 Hz, 1H), 2.51 (s, 3H), 2.39-2.32 (m, 2H), 2.32-2.25 (m, 1H), 2.25 (s, 6H), 1.87 (quint, J=6.9 Hz, 2H), 1.78 (q, J=12.4 Hz, 1H), 1.19 (t, J=7.3 Hz, 3H). LC/MS calculated for C$_{24}$H$_{35}$N$_5$O$_2$+H$^+$, 426.3; observed, 426.4.

Example 5

Preparation of (5R,8S,10R)-1,6-Dimethyl-8-aminomethyl-ergoline (10)

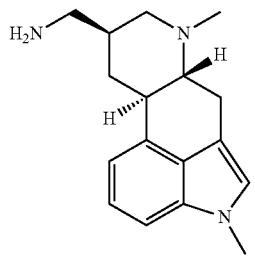 [SMILES: CN1C[C@H](CN)C[C@@H]2c3cccc4c3c(cn4C)C[C@H]21]

Metergoline (2.06 g, 5.11 mmol) was dissolved in methanol (50 mL) and 10% Pd/C was added (99 mg). The reaction mixture was stirred under a balloon filled with hydrogen for 2 h., filtered through celite, and concentrated under reduced pressure to afford 1.40 g of product as a slightly yellow, foamy solid. $^1$H NMR (400 MHz, CDCl$_3$): 7.19 (t, J=7.6 Hz, 1H), 7.11 (d, J=8.2 Hz, 1H), 6.92 (d, J=7.1 Hz, 1H), 6.72 (bs, 1H), 3.75 (s, 3H), 3.39 (dd, J=14.7, 4.3 Hz, 1H), 3.17-3.08 (m, 1H), 3.03-2.93 (m, 1H), 2.78-2.61 (m, 4H), 2.48 (s, 3H), 2.18-2.09 (m, 1H), 2.03-1.88 (m, 2H), 1.10 (q, J=12.1 Hz, 1H). $^{13}$C NMR (CDCl$_3$): 27.0, 32.2, 32.8, 39.4, 40.6, 43.4, 46.6, 61.8, 67.6, 106.7, 110.8, 112.6, 122.5, 122.7, 126.5, 133.6, 134.4. LC/MS calculated for C$_{17}$H$_{23}$N$_3$+H$^+$, 270.2; observed, 270.4.

Example 6

Preparation of (5R,8R,10R)-1,6-Dimethyl-ergoline-8-carboxylic acid methyl ester (13)

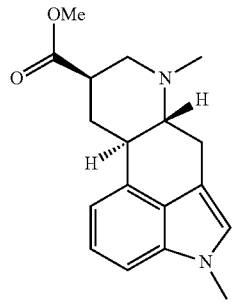 [SMILES: COC(=O)[C@@H]1C[C@@H]2c3cccc4c3c(cn4C)C[C@H]2N(C)C1]

Compound 10 (563.3 mg, 2.09 mmol), 4-formyl-1-methylpyridinium benzenesulfonate (1.033 g, 3.70 mmol), and anhydrous MgSO$_4$ (1.90 g) were stirred in CH$_2$Cl$_2$ (15 mL) and DMF (5 mL) for 75 min. After the MgSO$_4$ was removed by filtration, DBU (1.0 mL, 6.69 mmol) was added by syringe and stirring continued for 40 min. Next, a saturated solution of chilled aqueous oxalic acid (60 mL) was added and the reaction mixture was stirred for 45 min. The mixture was diluted with water (300 mL), neutralized with K$_2$CO$_3$, and extracted with CH$_2$Cl$_2$ (2×300 mL). The combined organic layers were dried (MgSO$_4$), filtered, and concentrated under reduced pressure to obtain 620.3 mg of crude aldehyde 12 as a black oil.

The aldehyde was dissolved in THF (18 mL) and methanol (18 mL). Ag$_2$O (2.21 g, 9.54 mmol) was added, followed quickly by 10% NaOH (6.00 mL). After 1 h, TLC analysis determined there was remaining aldehyde, so an additional 1.20 g of Ag$_2$O was added. After stirring an additional 15 min., the mixture was filtered and methanol (150 mL) and concentrated H$_2$SO$_4$ (10 mL) were added. The solution was left to stir overnight. The solution was diluted with water (500 mL), neutralized with NaHCO$_3$, and extracted with CH$_2$Cl$_2$ (2×400 mL). The combined organic layers were dried (MgSO$_4$), filtered, and concentrated under reduced pressure. Flash chromatography (CH$_2$Cl$_2$/methanol/NEt$_3$ 94:5:1, silica gel) furnished in 199 mg of 13 as a yellow solid (32% yield from metergoline). If not all aldehyde was oxidized prior to removal of the Ag$_2$O, this procedure also produced acetal 15 as a brown solid.

$^1$H NMR of 13 (400 MHz, CDCl$_3$): 7.19 (t, J=7.6 Hz, 1H), 7.12 (d, J=8.2 Hz, 1H), 6.93 (d, J=7.1 Hz, 1H), 6.73 (bs, 1H), 3.76 (s, 3H), 3.74 (s, 3H), 3.38 (dd, J=14.7, 4.3 Hz, 1H), 3.29-3.23 (m, 1H), 3.02-2.90 (m, 3H), 2.73-2.63 (m, 1H), 2.50 (s, 3H), 2.35 (t, J=11.5 Hz, 1H), 2.24-2.12 (m, 1H), 1.58 (q, J=13.1 Hz, 1H). $^{13}C$ NMR (CDCl$_3$): 26.9, 30.6, 32.8, 40.1, 41.5, 43.1, 51.8, 58.7, 66.8, 106.9, 110.5, 112.7, 122.6, 122.7, 126.4, 132.8, 134.4, 174.4. LC/MS calculated for $C_{18}H_{22}N_2O_2+H^+$, 299.2; observed, 299.3. $^1H$ NMR of 15 (400 MHz, CDCl$_3$): 7.19 (t, J=7.6 Hz, 1H), 7.11 (d, J=8.2 Hz, 1H), 6.95 (d, J=7.1 Hz, 1H), 6.73 (bs, 1H), 4.17 (d, J=7.3 Hz, 1H), 3.76 (s, 3H), 3.45-3.35 (m, 1H), 3.43 (s, 3H), 3.38 (s, 3H), 3.12-3.04 (m, 1H), 2.99-2.89 (m, 1H), 2.79-2.63 (m, 2H), 2.48 (s, 3H), 2.39-2.26 (m, 1H), 2.18-2.08 (m, 1H), 2.02 (t, J=11.4 Hz, 1H), 1.21 (q, J=12.5 Hz, 1H). LC/MS calculated for $C_{18}H_{22}N_2O_2+H^+$, 315.2; observed, 315.3.

Example 7

Preparation of (5R,8R,10R)-1,6-Dimethyl-N-[3-(dimethylamino)propyl]ergoline-8-carboxamide (14)

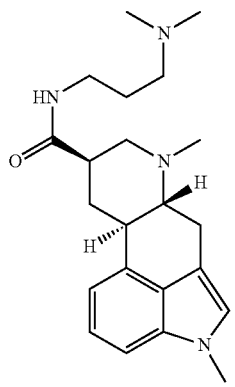 [SMILES: CN(C)CCCNC(=O)[C@@H]1C[C@@H]2c3cccc4c3c(cn4C)C[C@H]2N(C)C1]

Compound 13 (141.8 mg, 0.476 mmol), acetic acid (0.050 mL, 0.873 mmol), and 3-dimethylamino-1-propylamine (11.9 mmol) were heated in a microwave reactor to 120° C. for 20 h. The resulting gel was placed under vacuum 2 h and then suspended in 8 mL of saturated sodium bicarbonate solution and extracted with ethyl acetate (3×10 mL). The combined organic layers were dried (MgSO$_4$), filtered, and concentrated under reduced pressure. As NMR analysis showed some acetic acid and 3-dimethylamino-1-propylamine amine remaining, the material was suspended in 10 mL of aqueous K$_2$CO$_3$ solution and extracted with ethyl acetate (3×10 mL) The combined organic layers were dried (MgSO$_4$), filtered, and concentrated under reduced pressure to afford 14 as an orange solid (155.5 mg, 89% yield). $^1H$ NMR (400 MHz, CDCl$_3$): 7.62 (bs, 1H), 7.18 (t, J=7.6 Hz, 1H), 7.12 (d, J=8.2 Hz, 1H), 6.90 (d, J=7.0 Hz, 1H), 6.73 (bs, 1H), 3.76 (s, 3H), 3.44-3.35 (m, 3H), 3.22-3.14 (m, 1H), 3.00-2.92 (m, 1H), 2.86-2.78 (1H), 2.75-2.63 (2H), 2.49 (s, 3H), 2.43 (t, J=6.0 Hz, 2H), 2.37 (t, J=11.5 Hz, 1H), 2.26 (s, 6H), 2.24-2.15 (m, 1H), 1.72-1.60 (m, 3H). $^{13}C$ NMR (CDCl$_3$): 25.5, 27.0, 30.9, 32.8, 40.1, 40.3, 43.2, 43.7, 45.5, 59.4, 59.8, 66.9, 106.9, 110.6, 112.6, 122.6, 122.7, 126.4, 133.0, 134.4, 173.3. LC/MS calculated for $C_{22}H_{32}N_4O+H^+$, 369.3; observed, 369.4.

Example 8

Preparation of 1,6-Dimethylcabergoline (9)

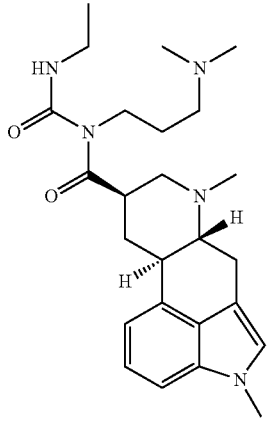 [SMILES: CCNC(=O)N(CCCN(C)C)C(=O)[C@@H]1C[C@@H]2c3cccc4c3c(cn4C)C[C@H]2N(C)C1]

Amide 14 (126.8 mg, 0.34 mmol) was dissolved in toluene (6 mL) and ethyl isocyanate was added (1.0 mL, 12.7 mmol). The reaction mixture was heated in a microwave reactor to 115° C. for 18 h and then concentrated under reduced pressure. The resulting residue was purified by chromatography (5% acetonitrile/water to 100% acetonitrile, C$_{18}$ column) to yield 62.1 mg yellow solid (41% yield).
$^1H$ NMR (400 MHz, CDCl$_3$): 9.43 (s, 1H), 7.17 (t, J=7.6 Hz, 1H), 7.11 (d, J=8.2 Hz, 1H), 6.8 (d, J=7.0 Hz, 1H), 6.73 (bs, 1H), 3.94-3.70 (m, 2H), 3.76 (s, 3H), 3.51-3.35 (m, 1H), 3.38 (dd, J=14.7, 4.3 Hz, 1H), 3.35-3.23 (m, 2H), 3.13-3.06 (m, 1H), 3.05-2.95 (m, 1H), 2.88-2.78 (m, 1H), 2.75-2.63 (m, 1H), 2.51 (t, J=11.2 Hz, 1H), 2.24 (s, 3H), 2.39-2.32 (m, 2H), 2.32-2.20 (m, 1H), 2.24 (s, 6H), 1.86 (quint, J=6.9 Hz, 2H), 1.77 (q, J=12.4 Hz, 1H), 1.19 (t, J=7.3 Hz, 3H). LC/MS calculated for $C25H_{37}N_5O_2+H^+$, 440.3; observed, 440.5.

Example 9

Effects of Cabergoline on Sexual Function in Rats. It was determined that the administration of cabergoline to rats had an acute effect that remained throughout the entire expanse of the test, as described herein. Specifically, male rats that were administered cabergoline ejaculated significantly more times than controls and had more intromissions before ejaculation with shorter ejaculation latencies. These results indicated that they were more vigorous copulators; reduced ejaculation latency with fewer intromissions before ejaculation would have indicated that cabergoline was possibility inducing a premature ejaculation state, whereas significantly more intromissions demonstrated that the rats were copulating at a faster rate. Additionally, rats administered cabergoline pursued the females more (hence had more intromissions) and their anticipatory level changes prior to copulation (a measure of their anticipatory desire) increased as well, suggesting that they were more behaviorally aroused in anticipation of sex. This correlates with the observation that the rats receiving cabergoline did not object to the gavage, in comparison with the controls, which objected to the gavage with typical vehemence (squealing, trying to kick the tube as is was inserted, etc.). The cabergoline rats may have found the sex more pleasurable, and therefore, did not object to the gavage. This can be tested by seeing whether it can potentiate the induction of a conditioned partner preference. For example, a study could be performed where rats take the drug immediately before their first sexual experience with an almond scented female and 4 days later the cabergoline rats are put in an open field with two females, one scented and the other unscented. Males given their first, e.g., 10, copulatory experiences with scented females would show a significant conditioned ejaculatory preference to ejaculate preferentially with the scented female. These results would indicate that cabergoline is embellishing the pleasure or reward induced by intromissions and especially ejaculations and would mean that the drug could be used medically to help men or women with orgasm dysfunction. Cabergoline could also be similarly tested on males that have had their ejaculations reduced to near zero by chronic administration of the SSRI fluoxetine. SSRIs are known to induce anorgasmia, and currently there is no treatment for this side effect. Thus, these studies suggest cabergoline may be used to treat sexual dysfunction (e.g., orgasm dysfunction, including, e.g., anorgasmia induced by SSRIs (e.g., fluoxetine)).

Example 10

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |

| (iv) Injection 1 (1 mg/ml) | mg/ml |
|---|---|
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula I:

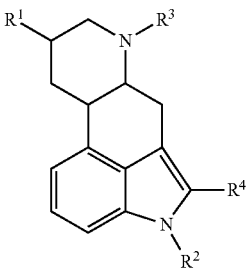

wherein:
$R^1$ is —C(=O)$NR_aR_b$;
$R^2$ is $(C_1-C_6)$alkyl;
$R^3$ is methyl;
$R^4$ is H, halo, —C(=O)$NR_hR_k$, —C(=O)OK, $(C_1-C_6)$alkyl, $(C_1-C_6)$alkanoyl, $(C_1-C_6)$alkoxycarbonyl, or $(C_1-C_6)$alkanoyloxy, wherein any $(C_1-C_6)$alkyl, $(C_1-C_6)$alkanoyl, $(C_1-C_6)$alkoxycarbonyl, or $(C_1-C_6)$alkanoyloxy can optionally be substituted with one or more halo, hydroxy, $(C_1-C_6)$alkoxy, $(C_1-C_6)$alkanoyl, $(C_1-C_6)$alkoxycarbonyl, $(C_1-C_6)$alkanoyloxy, or $NR_mR_n$;
$R_a$ is —C(=O)$NR_fR_g$;

$R_b$ is $(C_1$-$C_6)$alkyl that is substituted with one or more $NR_fR_g$;

$R_c$ is H, $(C_1$-$C_6)$alkyl, or aryl;

$R_f$ and $R_g$ are each independently H or $(C_1$-$C_6)$alkyl; or $R_f$ and $R_g$ together with the nitrogen to which they are attached form a heterocyclic ring;

$R_h$ and $R_k$ are each independently H, $(C_1$-$C_6)$alkyl or $(C_1$-$C_6)$alkanoyl, wherein any $(C_1$-$C_6)$alkyl or $(C_1$-$C_6)$alkanoyl can optionally be substituted with one or more $NR_fR_g$; or $R_h$ and $R_k$ together with the nitrogen to which they are attached form a heterocyclic ring; and $R_m$ and $R_n$ are each independently H or $(C_1$-$C_6)$alkyl; or $R_m$ and $R_n$ together with the nitrogen to which they are attached form a heterocyclic ring;

or a salt thereof.

2. The compound of claim 1 which is a compound of formula Ia:

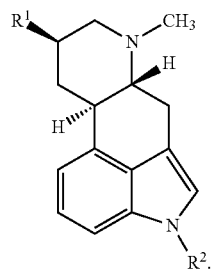

or a salt thereof.

3. A compound of formula I:

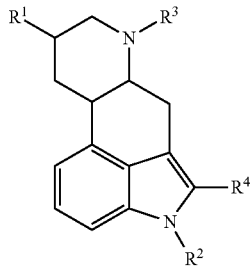

wherein $R^1$ is:

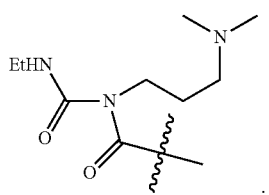

$R^2$ is $(C_1$-$C_6)$alkyl;

$R^3$ is methyl;

$R^4$ is H, —C(=O)$NR_hR_k$, —C(=O)$OR_c$, $(C_1$-$C_6)$ alkyl, $(C_1$-$C_6)$alkanol, $(C_1$-$C_6)$alkoxycarbonyl, or $(C_1$-$C_6)$alkanoyloxy, wherein any $(C_1$-$C_6)$alkyl, $(C_1$-$C_6)$alkanoyl, $(C_1$-$C_6)$alkoxycarbonyl, or $(C_1$-$C_6)$alkanoyloxy can optionally be substituted with one or more halo, hydroxy, $(C_1$-$C_6)$alkoxy, $(C_1$-$C_6)$alkanoyl, $(C_1$-$C_6)$alkoxycarbonyl, $(C_1$-$C_6)$alkanoyloxy, or $NR_mR_n$;

$R_c$ is H, $(C_1$-$C_6)$alkyl, or aryl;

$R_h$ and $R_k$ are each independently H, $(C_1$-$C_6)$alkyl or $(C_1$-$C_6)$alkanoyl, wherein any $(C_1$-$C_6)$alkyl or $(C_1$-$C_6)$alkanoyl can optionally be substituted with one or more $NR_fR_g$; or $R_h$ and $R_k$ together with the nitrogen to which they are attached form a heterocyclic ring; and $R_m$ and $R_n$ are each independently H or $(C_1$-$C_6)$alkyl; or $R_m$ and $R_n$ together with the nitrogen to which they are attached form a heterocyclic ring;

or a salt thereof.

4. A compound of formula I:

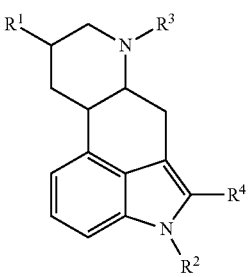

wherein $R^1$ is:

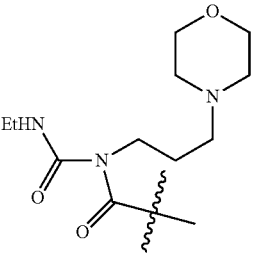

$R^2$ is H or $(C_1$-$C_6)$alkyl;

$R^3$ is methyl;

$R^4$ is H, halo, —C(=O)$NR_hR_k$, —C(=O)$OR_c$, $(C_1$-$C_6)$alkyl, $(C_1$-$C_6)$alkanoyl, $(C_1$-$C_6)$alkoxycarbonyl, or $(C_1$-$C_6)$alkanoyloxy, wherein any $(C_1$-$C_6)$alkyl, $(C_1$-$C_6)$alkanoyl, $(C_1$-$C_6)$alkoxycarbonyl, or $(C_1$-$C_6)$ alkanoyloxy can optionally be substituted with one or more halo, hydroxy, $(C_1$-$C_6)$alkoxy, $(C_1$-$C_6)$alkanoyl, $(C_1$-$C_6)$alkoxycarbonyl, $(C_1$-$C_6)$alkanoyloxy, or $NR_mR_n$;

$R_c$ is H, $(C_1$-$C_6)$alkyl, or aryl;

$R_h$ and $R_k$ are each independently H, $(C_1$-$C_6)$alkyl or $(C_1$-$C_6)$alkanoyl, wherein any $(C_1$-$C_6)$alkyl or $(C_1$-$C_6)$alkanoyl can optionally be substituted with one or more $NR_fR_g$; or $R_h$ and $R_k$ together with the nitrogen to which they are attached form a heterocyclic ring; and $R_m$ and $R_n$ are each independently H or $(C_1$-$C_6)$alkyl; or $R_m$ and $R_n$ together with the nitrogen to which they are attached form a heterocyclic ring;

or a salt thereof.

5. The compound of claim 1 wherein $R^2$ is $(C_1$-$C_6)$alkyl.

6. The compound of claim 1 wherein $R^2$ is methyl.

7. A pharmaceutical composition comprising a compound as described in claim 1 and a pharmaceutically acceptable diluent or carrier.

8. A compound which is:
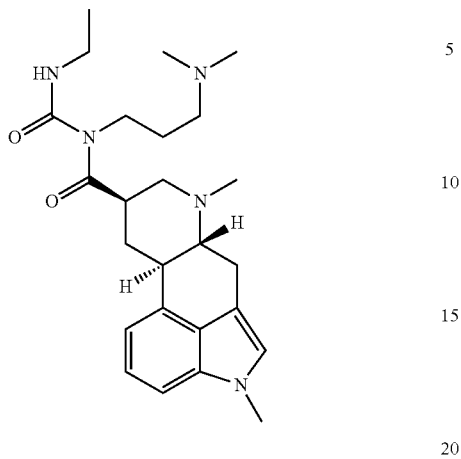
or a salt thereof.
9. A method for treating depression in an animal comprising administering a compound of formula I or a pharmaceutically acceptable salt thereof as described in claim 1 to the animal.
10. The method of claim 9 wherein the animal is human.
* * * * *

UNITED STATES PATENT AND TRADEMARK OFFICE
CERTIFICATE OF CORRECTION

PATENT NO. : 9,670,199 B2
APPLICATION NO. : 14/443576
DATED : June 6, 2017
INVENTOR(S) : Peter Dosa, Suck Won Kim and Michael Walters It is certified that error appears in the above-identified patent and that said Letters Patent is hereby corrected as shown below:

In the Claims

Column 22, Line 59, Claim 1, please delete "-C(=O)OK," and insert -- -C(=O)OR$_c$, -- therefor.

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*